(12) United States Patent
Jablokov et al.

(10) Patent No.: US 11,222,715 B2
(45) Date of Patent: Jan. 11, 2022

(54) METHOD OF CREATING NUTRITIONAL SUPPLEMENTS

(71) Applicants: Nicholai E. Jablokov, Radnor, PA (US); Eugene Igor Jablokov, Radnor, PA (US)

(72) Inventors: Nicholai E. Jablokov, Radnor, PA (US); Eugene Igor Jablokov, Radnor, PA (US)

( * ) Notice: Subject to any disclaimer, the term of this patent is extended or adjusted under 35 U.S.C. 154(b) by 0 days.

(21) Appl. No.: 17/183,902

(22) Filed: Feb. 24, 2021

(65) Prior Publication Data

US 2021/0183478 A1 Jun. 17, 2021

Related U.S. Application Data

(63) Continuation-in-part of application No. 16/000,873, filed on Jun. 5, 2018, now Pat. No. 10,959,453.

(60) Provisional application No. 62/560,015, filed on Sep. 18, 2017, provisional application No. 62/542,695, filed on Aug. 8, 2017, provisional application No. 62/515,373, filed on Jun. 5, 2017.

(51) Int. Cl.
*G16H 10/40* (2018.01)
*G16H 20/60* (2018.01)
*A23L 33/15* (2016.01)
*A61Q 19/00* (2006.01)
*A61K 8/67* (2006.01)

(52) U.S. Cl.
CPC ............. *G16H 10/40* (2018.01); *G16H 20/60* (2018.01); *A23L 33/15* (2016.08); *A61K 8/676* (2013.01); *A61K 2800/10* (2013.01); *A61K 2800/80* (2013.01); *A61Q 19/00* (2013.01)

(58) Field of Classification Search
CPC ........ G16H 10/40; G16H 20/60; G16H 50/70; A23L 33/15; A23L 33/16; A23L 33/30; A23L 5/30; A61K 8/676; A61K 2800/10; A61K 2800/80; A61Q 19/00; A23V 2250/1578; A23V 2250/16; A23V 2250/161; C02F 2103/08
See application file for complete search history.

(56) References Cited

U.S. PATENT DOCUMENTS

| 4,335,116 | A | * | 6/1982 | Howard | A61K 31/315 424/630 |
|---|---|---|---|---|---|
| 5,162,369 | A | * | 11/1992 | Ashmead | A61K 31/28 514/492 |
| 5,614,553 | A | * | 3/1997 | Ashmead | A61K 31/28 514/492 |
| 10,959,453 | B2 | * | 3/2021 | Jablokov | A23L 33/30 |
| 2007/0004639 | A1 | * | 1/2007 | Kane | A61K 31/685 514/183 |
| 2009/0246322 | A1 | * | 10/2009 | Lincoln | A23L 2/58 426/66 |
| 2009/0317488 | A1 | * | 12/2009 | Mehta | A61K 33/26 424/648 |
| 2012/0171130 | A1 | * | 7/2012 | Kennedy | A61K 36/81 424/49 |

(Continued)

*Primary Examiner* — Anthony J Weier

(57) ABSTRACT

A method of creating nutritional supplements including the steps of obtaining a customer's nutrient deficiency, calculating an ionic supplement composition based on the underlying element composition of the delivery product and the deficiency information, and mixing the ionic elements in dehydrated form with an appropriate liquid suspension.

18 Claims, 7 Drawing Sheets

(56) References Cited

U.S. PATENT DOCUMENTS

2015/0104424 A1* 4/2015 Scivoletto ............ A23K 20/147
424/93.4

* cited by examiner

METHOD OF CREATING NUTRITIONAL SUPPLEMENTS

PRIORITY CLAIM

Provisional applications No. 62/515,373, filed Jun. 5, 2017, 62/542,695, filed Aug. 8, 2017, and 62/560,015, filed Sep. 18, 2017, and non-provisional application Ser. No. 16/000,873 filed Jun. 5, 2018, are incorporated herein by reference in their entirety. This application claims the benefit of and priority to the above-mentioned provisional applications and non-provisional application, of which the present application is a continuation-in-part.

BACKGROUND

There is a great need for convenient nutritional supplements configured to be readily and fully absorbed by the cells and designed to cure specific and customer-specific nutritional deficiencies. In particular, there is a lack of nutritional supplements provided in non-conventional sources, such as health and beauty products, in part because of the difficulty in making nutrients in such mediums easily absorbable.

SUMMARY

The invention is directed toward infusion of minerals into products. More specifically, the invention is directed toward infusion of ionic minerals into personal care products and food products.

Ionic minerals are known to be beneficial for human health and wellbeing. There is a need for increased consumption of ionic materials, including ionic minerals.

However, ionic minerals are difficult to absorb by human cells, and must be formed in a water suspension. When doing so, positive and negative ions must be balanced, otherwise ions will separate from the water suspension, causing Fall-Out. Thus, it is required to provide the right amount of buffer, such as water. Buffer ratios differ for different types of mixtures and substances of products.

In accordance with an embodiment, provided is a proprietary blend of liquid ionic materials. The blend includes a customized liquid nutrient mix for individuals, with a blend of ionic vitamins and minerals. In accordance with an embodiment, the blend may be provided in liquid form, and customized for each customer, based on their unique nutrient deficiencies.

As disclosed herein, the proprietary blend of liquid ionic materials may be injected, mixed or infused into personal care products. Personal care products may include any suitable form of personal care products, including deodorants, lotions, body sprays, shampoos, soap, cleansers, face wash, lotions, balms, mouthwash, toothpaste, lip balm, hand sanitizers, or laundry detergent.

As disclosed herein, the proprietary blend of liquid ionic materials may be mixed into any suitable food product, and may be specifically formed for consumption by a human. Exemplary food products for mixing the blend of liquid ionic materials include condiments such as ketchup, hot sauce, or mustard, protein shakes, frozen pops, ice cream and any other suitable food.

The food products and personal care products are specially formed with the blend of ionic materials in order to prevent fall-out. Thus, the ions are prevented from reacting and colliding and thereby falling out of suspension. That is, the ionic materials are specifically formed to increase absorption rates by preventing fall-out.

In accordance with an embodiment, the invention utilizes natural oils, and liquids as a buffer, preferably formed above 50% to prevent reaction of the ionic minerals.

In accordance with the invention, wet and liquid products such as mouthwash or creams would be mixed in a similar fashion.

In accordance with an embodiment, the liquid ionic material preferably blends with other liquids, diluting in a liquid format. Thus, a buffer solution is formed.

For oils, dehydrated liquid ionic minerals are used. In an embodiment, the dehydrated form includes ionic crystals. In another embodiment, the dehydrated form includes ionic powders. It should be noted that dehydrated ionic minerals are extremely sensitive to moisture in the air, as well as temperature. Thus, great care must be taken avoid liquefying the dehydrated ions prior to use.

Thus, in accordance with the invention, water is used in an ionic mineral liquid suspension for personal care products such as shampoo, toothpaste, and creams, as well as for food items in liquid form, such as shakes. The water used in the suspension must be pure and free of contaminants such as fluoride, chloride, and other elements. That is, the suspension must be free and clear of trace elements with electromagnetic properties that would engage and bind with ionic minerals. Therefore, great care must be utilized to use a pure liquid suspension, one that is preferably distilled, and more preferably produced via double reverse-osmosis water purification process.

In an exemplary process, the ionic mineral mixture may be mixed with a desired product. The desired product may be formed in a first state, such as a gel. The gel may then be converted to a liquid, and at that stage receive the ionic mixture.

In another exemplary process, a desired product, such as a gel, may be specifically formulated as a liquid at first. In this liquid stage, the desired product may receive an ionic mineral mixture. After receiving the mixture, the desired product may then be converted to a gel form.

In yet another exemplary process, a liquid product may be packaged with the ionic mineral mixture already mixed in. In another example, a portion, such as 50%, of the ionic mineral mixture may be mixed into the liquid, in order to prevent full reactivity. The liquid may then be packaged with the additional 50% of ionic mineral mixture, to be added in by the user before consumption.

In another example, the liquid may be packaged without any ionic mineral mixture mixed in. In an additional package, sold or packaged with the liquid, a pre-measured amount of ionic mineral mixture may be provided, to be mixed in prior to, or immediately prior to use. Examples of prior to use or immediately prior to use include the week before use, day before use, day of use, morning of use, an hour before use, thirty minutes before use, five minutes before use, one minute before use, or any other suitable time period.

It should be noted that use as disclosed herein may contemplate the initial use, such as for a bottle of mouthwash. That is, the ionic mineral mixture may be mixed with the full bottle of mouthwash (which may be used over a span of days, months or even years). In another embodiment, the ionic mineral mixture may be provided with single use measurements, or may include a device to measure single use measurements, such that the ionic mineral mixture may be added to each serving of liquid prior to use.

In another embodiment, the liquid may be mixed with the ionic mineral mixture before packaging. However, the ionic mineral mixture may include a coating to prevent reactivity of the minerals prior to use. For example, the coating may be specifically formed to dissolve only upon reacting with the acidity of the human mouth or stomach, at a specified pH level.

In accordance with the invention, the ionic material solution must be kept free of fungal or bacterial growth.

The ionic mineral solution, as noted above, should be formulated specifically for its intended recipient. The ionic mixture is therefore personalized for an individual due to their specific health needs. That is, the ionic mixture is customized with specific vitamins and minerals depending on the recipient's health, activity levels, or other desirable qualities. For example, an individual engaged in competitive sports may desire more vitamin B6 for energy, whereas those with iron deficiencies may desire iron in increased quantities. The needs may be determined utilizing blood, hair, or urine analysis. Additionally, DNA testing may be performed, and/or sleep analysis, weight analysis, exercise statistics, and/or a full health workup may be utilized.

A baseline nutrient level for each specific recipient, based on characteristics such as age, gender, build, family history, ethnicity, or any other parameters may be utilized. Variations may be implemented for qualities such as activity level or family history or disposition. Nutrients may then be added to the nutrient mix in the form of liquid ionic vitamins and minerals. In turn, this can be absorbed at high levels, due to the ionic nature.

In accordance with an embodiment, a recipient may specify a desire for ionic mouthwash. The ionic solution may then be provided, based on the recipient's pre-received standard nutrient profiles. The ionic solution may then be specifically formulated for mixture with the mouthwash, based on the composition of the mouthwash. The mouthwash may either be combined with the ionic material solution before shipping to the recipient, or may be sent in a container separate from the ionic solution, and combined immediately prior to use.

For a human cell to absorb ionic minerals, ionic ions must be held in a water suspension. However, the positive and negative ions must be balanced or the ions will separate from the water suspension in a process called "Fall-Out". For the ions to be held in a suspension, the right amount of buffer is required—in this case, the buffer is water. Different ionic minerals require different buffer rations. Iron requires a larger buffer ration than magnesium or potassium. Potassium, for example, requires a buffer of 50% water or it will combine with other ions such as ionic magnesium or calcium. When potassium combines with ionic magnesium, it forms a compound and leaves the suspension. Similarly, calcium and potassium ions form crystals upon collusion, and therefore must be properly and separately integrated into the suspension. The ionic minerals should not be mixed directly in even a proportionate amount of water because of their tendency for initial engagement may. Instead, each ionic mineral type must first be introduced to a separate and proportionate water supply. The resultant suspensions may then be combined.

That absorption rate for compounds under fall-out is as low as 5%. When pills of magnesium or other minerals are added to water, unless control is exerted to balance and proportion, absorption rates will be similarly low. Therefore, it is advantageous to provide to customers ionic minerals already engaged in a water suspension according to ideal absorption parameters.

The water used in the suspension must be pure and free of contaminants like fluoride, chloride, and other elements. These trace elements, commonly found in acceptable quantities in tap water, have electromagnetic properties that may lead to engagement and binding with the ionic minerals. The resultant ionic bonds may disrupt the positive and negative ionic balance. Therefore, the water used should be distilled, and ideally, produced or clarified via a double reverse osmosis water machine.

Many micro-organisms feed on minerals, including ionic minerals, for energy and development and rely on the water mixture to propagate. Therefore, ionic materials in liquid form also need Vitamin C in order to prevent fungal or bacterial growth. Vitamin C also helps control the pH levels, which is a factor in determining molecular engagement. Accordingly, there must be an appropriate ratio of ionic mineral to vitamin C in order to preserve the fidelity and integrity of the supplement for human consumption.

Even a perfectly balanced and enriched ionic mineral liquid supplement is imperfect unless it is defined and designed for its recipient. In particular, the ionic mineral mixture should provide the minerals that the individual either lacks or is in increased need of due to health and illness conditions. Alternatively, individuals engaged in competitive sports or recreation may need a surplus of minerals otherwise found in acceptable limits. To determine these needs, the blood, hair, and urine should be obtained and analyzed. Additional relevant observations and/or analyses may include weight, sleep quality and quantity, and exercise statistics such as those obtained from a pedometer.

Results for individuals may be compared with standard nutrient profiles based on age, gender, and other parameters. Where an individual's giving nutrient number is deficient, the corresponding nutrient can be added to a nutrient mix in the form liquid ionic minerals. These liquid ionic minerals may be provided in a transportable form, such as a gallon jug or set of individual bottles or containers. The mixture can be provided on a recurring basis, such as weekly, monthly, or bi-monthly. The components of the mixture can be updated based on additional tests, nutritional data, and exercise statistics. Results may be communicated electronically by one or more devices to a central processor and database, whereupon standard comparison and nutritional deficiency calculations may be iterated.

Ionic minerals may be mixed at room temperature and atmospheric pressure. For adequate mixing without introducing turbulence-derived energy content, a magnetic mixer may be used to fill the containers. Ionic minerals may be purchase from commercial suppliers or manufactured prior to mixing.

The invention is directed toward infusion of minerals into products. More specifically, the invention is directed toward infusion of ionic minerals into personal care products and food products.

In accordance with an embodiment, provided is a proprietary blend of dehydrated liquid ionic materials. The blend includes a customized liquid nutrient mix for individuals, in dehydrated form with a blend of ionic vitamins and minerals. In accordance with an embodiment, the blend may be provided in solid, dehydrated form, and customized for each customer, based on their unique nutrient deficiencies. The dehydrated form may be formed as a powdered solid, which may be ideal for mixing with both liquids and solids.

As disclosed herein, the proprietary blend of dehydrated liquid ionic materials may be mixed or infused into personal care products. Personal care products may include any suitable form of personal care products, including deodorants, lotions, creams, body sprays, shampoos, soap, cleansers, face wash, lotions, balms, mouthwash, toothpaste, lip balm, hand sanitizers, or laundry detergent.

As disclosed herein, the proprietary blend of dehydrated liquid ionic materials may be mixed into any suitable food product, and may be specifically formed for consumption by a human. Exemplary food products for mixing the blend of dehydrated liquid ionic materials include condiments such as ketchup, hot sauce, or mustard, protein shakes, frozen pops, ice cream and any other suitable food.

The food products and personal care products are specially formed with the blend of dehydrated ionic materials in order to prevent fall-out. Thus, the ions are prevented from reacting and colliding and thereby falling out of suspension. That is, the ionic materials are specifically formed to increase absorption rates by preventing fall-out.

In accordance with an embodiment, the invention utilizes dehydrated ionic minerals as a buffer, preferably formed above 50% to prevent reaction of the ionic minerals.

Ionic minerals formed in a dehydrated fashion are particularly suited for storing the ionic material. Additionally, the dehydrated nature reduces weight and space requirements of storage. Moreover, the versatility of dehydrated ionic minerals allows it to be mixed with both liquids and solids.

In order to process the ionic material into a dehydrated state, a dehydration reaction is performed. A dehydrating agent is used, and the result is dehydrated liquid ionic minerals.

Dehydrated liquid ionic minerals are then slowly mixed with a desired food or cosmetic/personal care product. Mixing is performed by any suitable mixer, such as a standard mixing machine. For example, a kitchen mixer may be used. In one embodiment, a slow speed is used, to allow each added mineral to mix properly. In an embodiment, each mineral added requires approximately 15 minutes. In other embodiments, any suitable time frame, such as 1 minute, 5 minutes, 20 minutes, or 30 minutes may be utilized.

Thus, in accordance with the invention, water is used in an ionic mineral liquid suspension for personal care products such as shampoo, toothpaste, and creams, as well as for food items in liquid form, such as shakes. The water used in the suspension must be pure and free of contaminants such as fluoride, chloride, and other elements. That is, the suspension must be free and clear of trace elements with electromagnetic properties that would engage and bind with ionic minerals. Therefore, great care must be utilized to use a pure liquid suspension, one that is preferably distilled, and more preferably produced via double reverse-osmosis water purification process. This process may then be dehydrated using a dehydration reaction, to produce a dehydrated product.

In an exemplary process, the ionic mineral mixture may be mixed with a desired product. The desired product may be formed in a first state, such as a dehydrated material. The dehydrated material may then be converted to a liquid, by adding a predetermined amount of liquid, and at that stage receive the ionic mixture.

In another exemplary process, a desired product, such as a gel, may be specifically formulated as a liquid at first. In this liquid stage, the desired product may receive an ionic mineral mixture. After receiving the mixture, the desired product may then be converted to a dehydrated form.

In yet another exemplary process, a dehydrated product may be packaged with the ionic mineral mixture already mixed in. In another example, a portion, such as 50%, of the ionic mineral mixture may be mixed into the liquid, in order to prevent full reactivity. The liquid may then be dehydrated, and then packaged with the additional 50% of ionic mineral mixture, to be added in by the user before consumption. The additional 50% added in later may include sufficient liquid to also implement a hydration reaction, in order to re-hydrate the dehydrated mixture.

In another example, a liquid or gel may be packaged without any ionic mineral mixture mixed in. In an additional package, sold or packaged with the liquid or gel, a pre-measured amount of dehydrated ionic mineral mixture may be provided, to be mixed in prior to, or immediately prior to use. Examples of prior to use or immediately prior to use include the week before use, day before use, day of use, morning of use, an hour before use, thirty minutes before use, five minutes before use, one minute before use, or any other suitable time period.

It should be noted that use as disclosed herein may contemplate the initial use, such as for a bottle of mouthwash. That is, the ionic mineral mixture may be mixed with the full bottle of mouthwash (which may be used over a span of days, months or even years). In another embodiment, the ionic mineral mixture may be provided with single use measurements, or may include a device to measure single use measurements, such that the ionic mineral mixture may be added to each serving of liquid prior to use.

In another embodiment, the liquid may be mixed with the dehydrated ionic mineral mixture before packaging. However, the dehydrated ionic mineral mixture may include a coating to prevent reactivity of the minerals prior to use. For example, the coating may be specifically formed to dissolve only upon reacting with the acidity of the human mouth or stomach, at a specified pH level.

In accordance with the invention, the dehydrated ionic material solution must be kept free of fungal or bacterial growth. More specifically, the dehydrated form may be preferred, in an embodiment, for preventing growth of fungus or bacteria.

The dehydrated ionic mineral solution, as noted above, should be formulated specifically for its intended recipient. The dehydrated ionic mixture is therefore personalized for an individual due to their specific health needs. That is, the dehydrated ionic mixture is customized with specific vitamins and minerals depending on the recipient's health, activity levels, or other desirable qualities. For example, an individual engaged in competitive sports may desire more vitamin B6 for energy, whereas those with iron deficiencies may desire iron in increased quantities. The needs may be determined utilizing blood, hair, or urine analysis. Additionally, DNA testing may be performed, and/or sleep analysis, weight analysis, exercise statistics, and/or a full health workup may be utilized.

A baseline nutrient level for each specific recipient, based on characteristics such as age, gender, build, family history, ethnicity, or any other parameters may be utilized. Variations may be implemented for qualities such as activity level or family history or disposition. Nutrients may then be added to the nutrient mix in the form of liquid ionic vitamins and minerals. In turn, this can be absorbed at high levels, due to the ionic nature.

In accordance with an embodiment, a recipient may specify a desire for ionic shampoo. The dehydrated ionic solution may then be provided, in a dehydrated form, based on the recipient's pre-received standard nutrient profiles. The ionic solution may then be specifically formulated for mixture with the shampoo, based on the composition of the recipient's preferred shampoo. Additionally, the dehydrated ionic solution may be specifically formulated to be rehydrated when added to the shampoo. The shampoo may either be combined with the dehydrated ionic material solution before shipping to the recipient, or may be sent in a container separate from the ionic solution, and combined immediately prior to use.

The dehydrated form may be applied to cereals, bars, or other dry goods. They may be added after the dry goods have been manufactured or during manufacture. Alternately, the liquid form may be applied and then dehydrated once applied to the dry goods.

Ionic magnesium or other ionic materials should be placed in an incubator, under a spray dryer, or in an oven with heated fans to evaporate the liquid. This dehydration ideally occurs in a "bubble" or housing designed to keep moisture out. Ideally, moisture is less than 10%. A prefabricating cooling coil assembly may be mounted on an aluminum plate connected to a Munters HC-150 dehumidifier. The coil should have a garden hose connection connected to a recirculating chiller with the specs of ⅓ HP, 1000 W, 14 L/minute, 115 V. This setup permits cool, dehumidified air to blow in a controlled environment, which is perfect for encapsulating dehydrated liquid ionic minerals.

DETAILED DESCRIPTION

Figure 1:
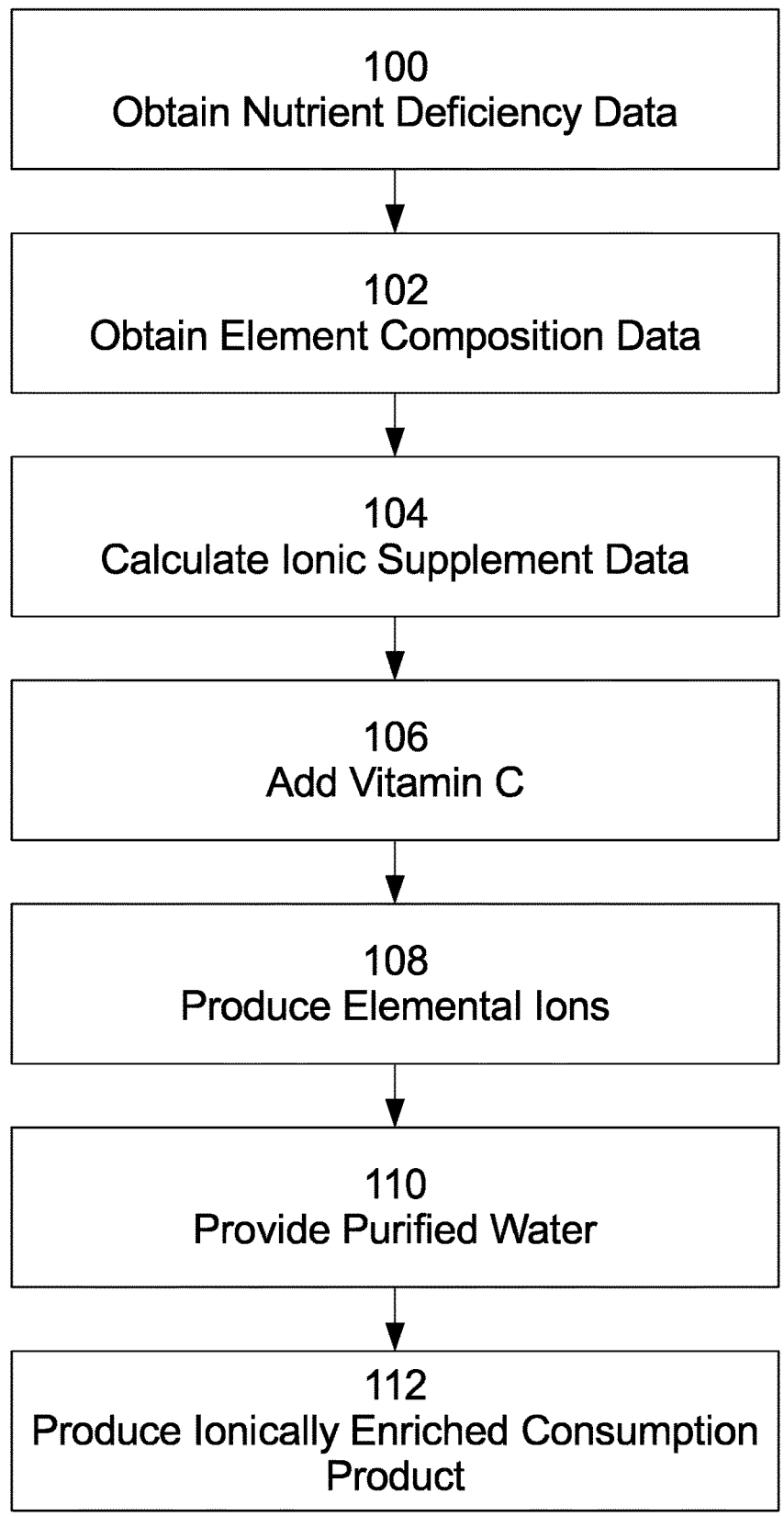
FIG. 1 shows an exemplary method flowchart.

As shown in FIG. 1, a customer's nutrient deficiency data is obtained 100. Also, the element composition data for the intended product is obtained 102. The ionic supplement data is calculated 104 by determining the difference between the element composition and the deficiency data. Vitamin C may be added 106 in either dehydrated form with the ionic material or in the liquid suspension in order to prevent corruption. Ionic material may be produced through either dehydration, or a condensation/hydration reaction 108. Vitamin C, together with ionic material, may be added to purified water 110. They are then combined into the ionically enriched consumption product 112.

Figure 2:
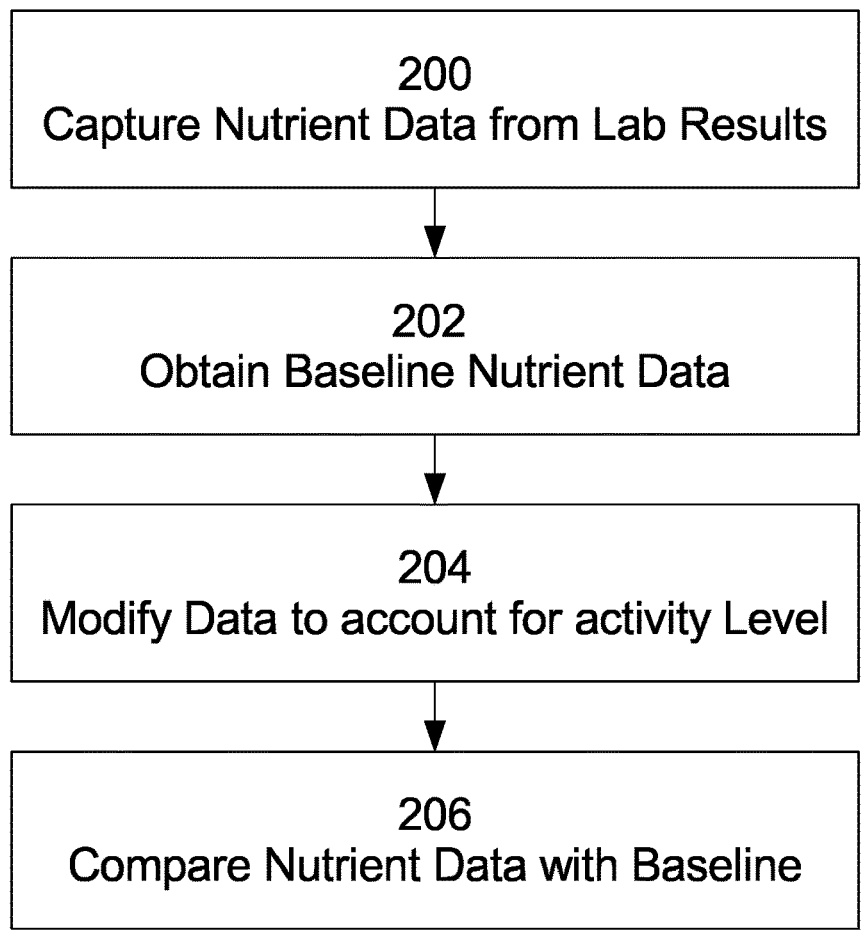
FIG. 2 shows an exemplary method flowchart.

As shown in FIG. 2, nutrient deficiency data is determined by comparing a customer's nutrient information to a baseline 200. The customer's nutrient information may first be capturing from blood, hair, or urine tests. This nutrient information is compared 206 to a baseline of nutrient information appropriate to the person based on their age, gender, built, ethnicity, and family history, which may be located in a database 202. The baseline nutrient information may be modified, for comparison's sake, using other information obtained from the person, such as his or her activity level, as established using exercise statistics 204. The baseline data is compared to the nutrient information to determine the nutrients in deficiency.

Figure 3:
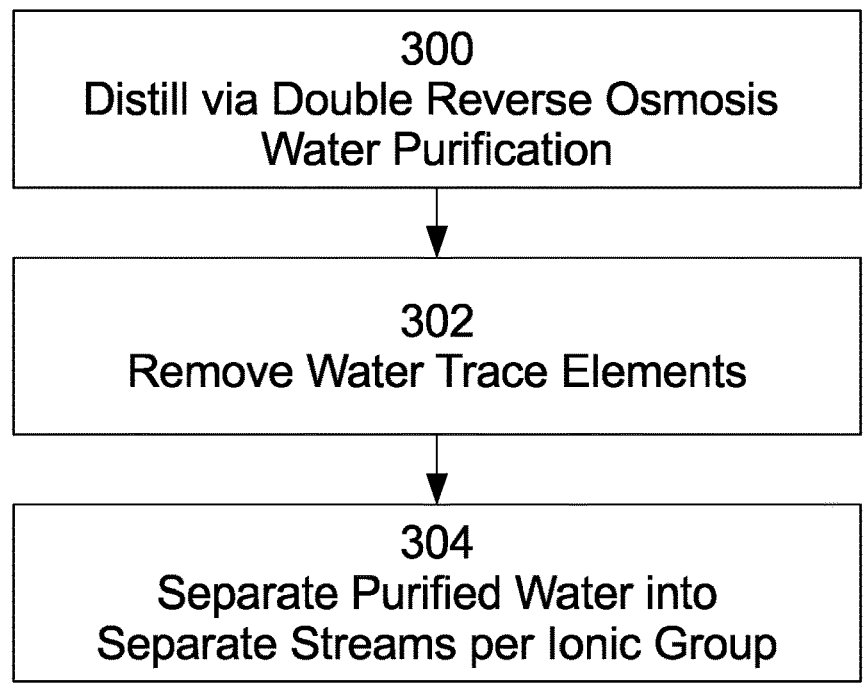
FIG. 3 shows an exemplary method flowchart.

In order to determine how much nutrients need to be added to a product to account for the nutrient deficiency, the nutrients already in the product need to be determined—thus, the element composition of a product is obtained 102. In addition, since the ionic supplement information may be corrupted by microbial growth, Vitamin C may be added in the correct proportion 106. The ionic material, including the Vitamin C, may be added to purified water. As shown in FIGS. 1 and 3, Purified water may be obtained 108 using a double reverse-osmosis water purification process 300. Importantly, trace elements with electromagnetic properties that would engage and bind with the ionic minerals must be removed 302. In certain cases, where the ionic minerals would react with each other, they are added to separate liquid suspensions 304.

Figure 4:
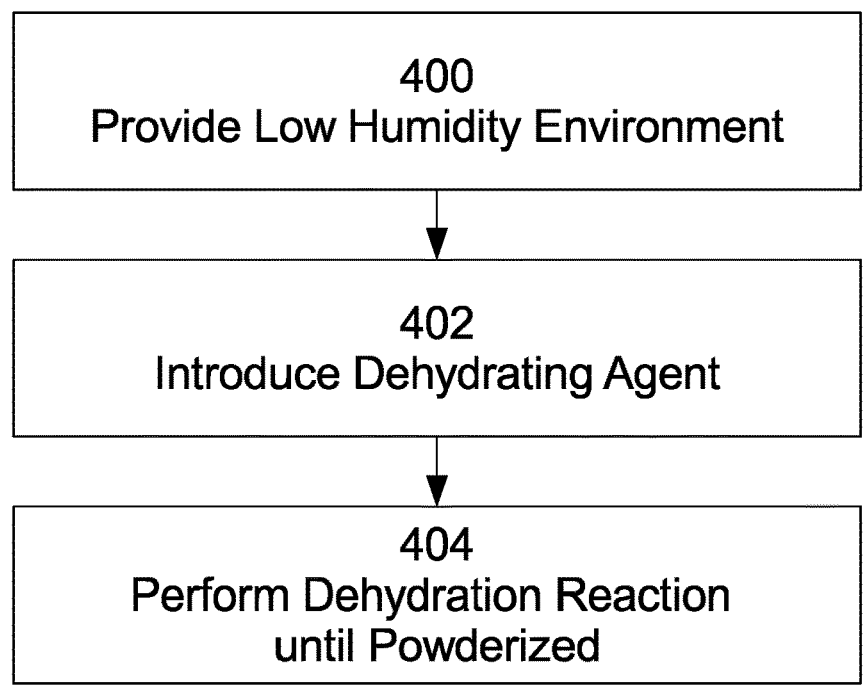
FIG. 4 shows an exemplary method flowchart.

As shown in FIG. 4 before adding ionic minerals to the liquid suspension, they should be dehydrated, or provided in dehydrated form. Ionic material should be dehydrated in a low humidity environment 400, with no more than 30% humidity, preferably 10% or less. This low humidity environment may be created via a "bubble" or sealed area. This bubble may be a workspace designed to house a human worker or merely enough space for a machine to operate and may therefore be called a spatial work bubble. The actual dehydration reaction, which may include a dehydrating agent 402, may take place in a dehydrator oven or a spray dryer may be applied until powderized 404.

Figure 5:
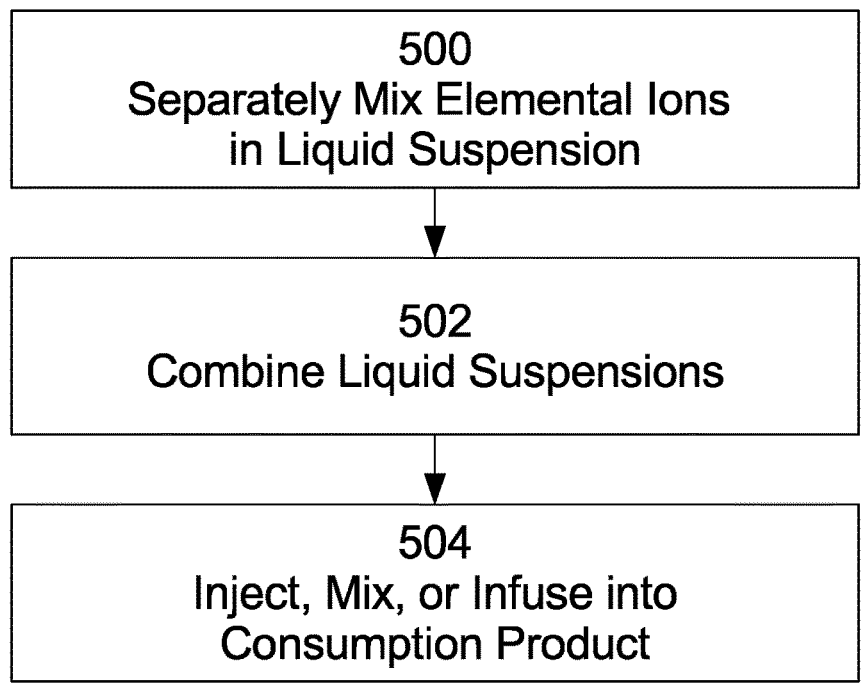
FIG. 5 shows an exemplary method flowchart.

As shown in FIG. 5, the ionic minerals and liquid suspension may be mixed together using a magnetic mixer at room temperature and atmospheric pressure. Again, each ionic mineral may be mixed in its own liquid suspension before combining 500 before being combined with the liquid suspension of other ionic minerals 502. The liquid ionic mixture may then be injected, mixed, or infused into a consumption product 504. Instead of mixing the dehydrated ionic material into a liquid, they may instead by encapsulated into pills.

Figure 6:
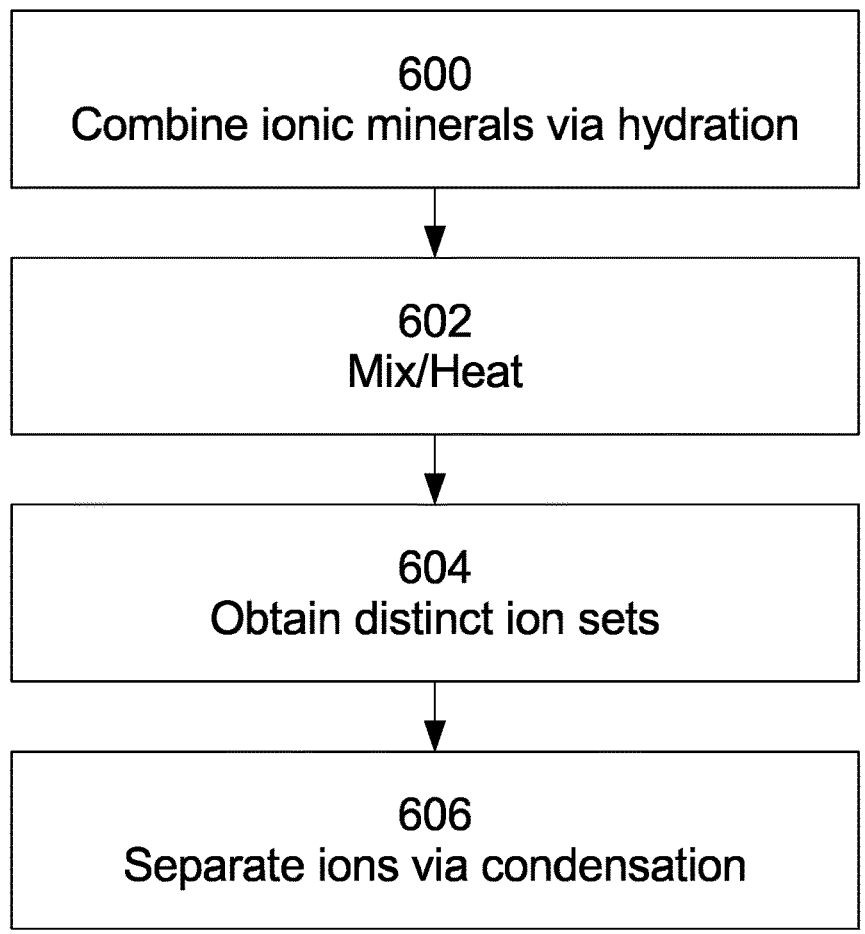
FIG. 6 shows an exemplary method flowchart.

As shown in FIG. 6, ionic minerals may be created via a hydration and condensation reaction. Minerals that have ionic potential may combined through hydration 600. The hydrated ions may then be mixed or heated in order to increase the energy level 602 in order to yield distinct ion sets 604. The distinct ion sets may then be separated through condensation 606 such that one distinct ion set condenses whereas the other distinct ion set does not. Other methods of producing ionic minerals through hydration and condensation steps are also contemplated.

Figure 7:
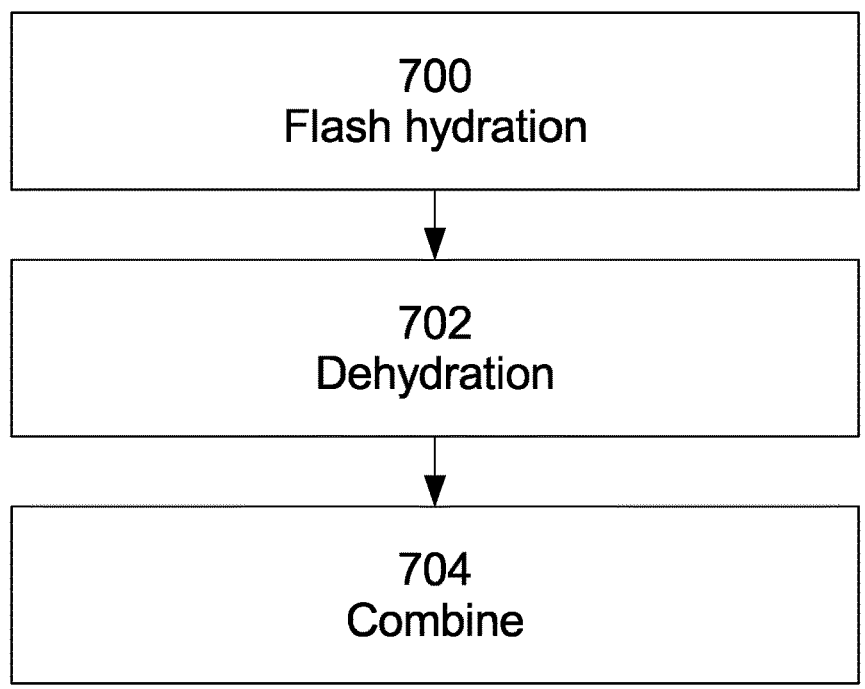
FIG. 7 shows an exemplary method flowchart.

As shown in FIG. 7, ionic minerals may have their crystallization changed through a flash hydration step 700, followed by a dehydration step 702. The crystallization change may decrease the reactivity of the ionic minerals so that they can be combined 704 with other ionic minerals without reacting to each other.

The production of ionic material through dehydration may occur in a spatial work bubble having less than 10% humidity, or through hydration and condensation in a spatial work bubble having between 10-60% humidity.

The invention claimed is:

1. A method of creating customized ionic mineral enriched consumption products, including the steps of:
   a. determining nutrient deficiency data for an individual by comparing nutrient data from the individual with matching demographic data;
   b. obtaining element composition of a product;
   c. calculating ionic supplement data using the nutrient deficiency data and the element composition of the product, the ionic supplement data including ionic element composition and proportion data;
   d. producing first ions and second ions using the ionic supplement data and by performing a condensation or hydration reaction on ionic minerals to alter crystallization;
   e. separately mixing the first ions into a first liquid suspension and the second ions into a second liquid suspension, with the concentration of the first and second ions in the first and second liquid suspension based on the ionic supplement data;

f. combining the first liquid suspension and the second liquid suspension into a single liquid ionic mixture;

g. injecting, mixing, or infusing the single liquid ionic mixture into the consumption product.

2. The method of claim 1, the condensation or hydration reaction occurring in a spatial work bubble having less than 10% humidity.

3. The method of claim 2, the condensation or hydration reaction occurring in a spatial work bubble having between 10-60% humidity.

4. The method of claim 1, producing the first or second ions by dehydrating liquid ionic minerals until the liquid ionic minerals are powderized.

5. The method of claim 1, where matching demographic data comprises data of other individuals having the same gender, age, ethnicity, or family history.

6. The method of claim 1, the first or second ions being anionic ions.

7. The method of claim 1, the first or second ions being cationic ions.

8. The method of claim 1, the first or second ions being alkali metals or alkali earth metals.

9. The method of claim 1, the first or second ions being transition metals.

10. The method of claim 1, the first or second ions being non-metals.

11. The method of claim 1, the first or second ions being halogens.

12. The method of claim 1, the first or second ions being ionic compounds.

13. The method of claim 1, the first or second liquid suspensions produced by removing from water trace elements with electromagnetic properties that would engage and bind ionic minerals.

14. The method of claim 1, including the additional step of calculating a second set of ionic supplement data using the first set of ionic supplement data and a Vitamin C to ionic mineral ratio of between 1-100 mg of Vitamin C to 10 grams of ionic minerals.

15. The method of claim 1, including the additional step of additionally calculating the ionic supplement data using the ionic supplement data and a Vitamin C to ionic mineral ratio of between 100-200 mg of Vitamin C to 10 grams of ionic minerals.

16. A method of creating customized ionic mineral enriched consumption products, including the steps of:

a. calculating ionic supplement data to be added to a product for an individual using nutrient deficiency data from the individual and element composition of the consumption product;

b. separately mixing the first ions into a first liquid suspension and the second ions into a second liquid suspension, with the concentration of the first and second ions in the first and second liquid suspension based on the ionic supplement data;

c. combining the first liquid suspension and the second liquid suspension into a single liquid ionic mixture;

d. injecting, mixing, or infusing the single liquid ionic mixture into the consumption product;

e. producing the first or second ions by performing a condensation or hydration reaction on ionic minerals to alter crystallization.

17. The method of claim 1, including the additional step of calculating the ionic supplement data using the ionic supplement data and a Vitamin C to ionic mineral ratio of between 1-200 mg of Vitamin C to 10 grams of ionic minerals.

18. A method of creating customized ionic mineral enriched consumption products, including the steps of:

a. calculating ionic supplement data to be added to a product for an individual using nutrient deficiency data from the individual, element composition of the consumption product, and a Vitamin C to ionic mineral ratio of between 1-200 mg of Vitamin C to 10 grams of ionic minerals;

b. producing ions by performing a condensation or hydration reaction on ionic minerals to alter crystallization;

c. Adding the ions into a liquid suspension with the concentration of the ions based on the ionic supplement data;

d. injecting, mixing, or infusing the ionic liquid suspension mixture into the consumption product.

* * * * *